US008945929B2

(12) United States Patent
Tanigawara et al.

(10) Patent No.: US 8,945,929 B2
(45) Date of Patent: Feb. 3, 2015

(54) MARKER FOR DETERMINATION OF SENSITIVITY TO ANTI-CANCER AGENT (75) Inventors: Yusuke Tanigawara, Tokyo (JP); Mitsuhiro Watanabe, Tokyo (JP); Eri Arita, Tokyo (JP); Akito Nishimuta, Tokyo (JP); Yasuko Yamayoshi, Tokyo (JP); Takeshi Matsuzaki, Tokyo (JP); Shinji Sugimoto, Tokyo (JP)

(73) Assignees: Keio University, Tokyo (JP); Kabushiki Kaisha Yakult Honsha, Tokyo (JP)

( * ) Notice: Subject to any disclaimer, the term of this patent is extended or adjusted under 35 U.S.C. 154(b) by 517 days.

(21) Appl. No.: 12/865,725

(22) PCT Filed: Jan. 30, 2009

(86) PCT No.: PCT/JP2009/000358
§ 371 (c)(1),
(2), (4) Date: Aug. 1, 2010

(87) PCT Pub. No.: WO2009/096189
PCT Pub. Date: Aug. 6, 2009

(65) Prior Publication Data
US 2011/0003842 A1  Jan. 6, 2011

(30) Foreign Application Priority Data
Jan. 31, 2008  (JP) ................................ 2008-021123

(51) Int. Cl.
G01N 33/48  (2006.01)
G01N 33/53  (2006.01)
A61K 31/4745  (2006.01)
A61K 45/06  (2006.01)
G01N 33/50  (2006.01)
G01N 33/68  (2006.01)

(52) U.S. Cl.
CPC ............. A61K 31/4745 (2013.01); A61K 45/06 (2013.01); G01N 33/5011 (2013.01); G01N 33/6812 (2013.01); G01N 2800/52 (2013.01); Y10S 436/813 (2013.01)
USPC ............................... 436/63; 436/64; 436/813

(58) Field of Classification Search
USPC .............................................. 436/63, 64, 813
See application file for complete search history.

(56) References Cited

U.S. PATENT DOCUMENTS

2007/0071762 A1  3/2007  Ts'o et al.

FOREIGN PATENT DOCUMENTS

WO  WO 2008036691 A2 *  3/2008

OTHER PUBLICATIONS

Ishii et al.; "L-[1-13C] Phenylalanine Breath Test Reflects Histological Changes in the Liver"; 2003; Journal of Surgical Research; 114: 120-125.*
Meadows et al.; "Interaction between specific dietary factors and experimental chemotherapy of metastatic melanoma"; 1986; Cancer Chemother. Pharmacol.; 16: 229-236.*
Agrawal et al.; "Gem 231, a second-generation antisense agent complementary to protein kinase A Rlalpha subunit, potentiates antitumor activity of irinotecan in human colon, pancreas, prostate and lung cancer xenografts."; 2002; Int. J. Oncol; 21(1): 65-72; PubMed abstract; PMID: 12063551.*
Steenkeste, K. et al., "Camptothecins-guanine interactions: mechanism of charge transfer reaction upon photoactivation", Chemical Physics, vol. 275, No. 1-3, pp. 93-108, (2002).
Shimada, Yasuhiro at al., "Phase II Study of CPT-11, a New Camptothecin Derivative, in Metastatic Colorectal Cancer", Journal of Clinical Oncology, vol. 11, No. 5, pp. 909-913, (May 1993).
Cunningham, David at al., "A Phase III Study of Irinotecan (CPT-11) Versus Best Supportive Care in Patients With Metastatic Colorectal Cancer Who Have Failed 5-Fluorouracil Therapy", Seminars in Oncology, vol. 26, No. 1, Suppl 5, pp. 6-12, (Feb. 1999).
Rougier, Philippe at al., "Randomised trial of irinotecan versus fluorouracil by continuous infusion after fluorouracil failure in patients with metastatic colorectal cancer", The Lancet, vol. 352, pp. 1407-1412, (Oct. 31, 1998).
Pitot, H.C. et al., "N9841: A randomized phase III equivalence trial of irinotecan (CPT-11) versus oxaliplatin/5-fluorouracil (5FU)/leucovorin (FOLFOX4) in patients (pts) with advanced colorectal cancer (CRC) previously treated with 5FU", Journal of Clinical Oncology, 2005 ASCO Annual Meeting Proceedings, vol. 23, No. 16S, Part 1 of II (Jun. 1 Supplement), (2005):, 3506.
Saltz, B. Leonard at al., "Irinotecan Plus Fluorouracil and Leucovorin for Metastatic Colorectal Cancer", The New England Journal of Medicine, vol. 343, No. 13, pp. 905-914, (Sep. 28, 2000).
Douillard, JY et al,, "Irinotecan combined with fluorouracil compared with fluorouracil alone as first-line treatment for metastatic colorectal cancer: a multicentre randomized trial", The Lancet, vol. 355, pp. 1041-1047, (Mar. 2000).
Kawato, Yasuyoshi et al., Intracellular Roles of SN-38, a Metabolite of the Camptothecin Derivative CPT-11, in the Antitumor Effect of CPT-11, Cancer Research, vol. 51, pp. 4187-4191, (Aug. 15, 1991).
Cecchin, Erika et al., "Carboxylesterase Isoform 2 mRNA Expression in Peripheral Blood Mononuclear Cells is a Predictive Marker of the Irinotecan to SN38 Activation Step in Colorectal Cancer Patients", Clin., Cancer Res., vol. 11, No. 19, pp. 6901-6907, (Oct. 1, 2005).
Tanimoto, Kenji et al., "Human carboxylesterase 1A2 expressed from carboxylesterase 1A1 and 1A2 genes is a potent predictor of CPT-11 cytotoxicity in vitro", Pharmacogenetics and Genomics, vol. 17, No. 1, pp. 1-10, (2007).
Potti, Anil et al., "Genomic signatures to guide the use of chemotherapeutics", Nature Medicine, vol. 12, No. 11, pp. 1294-1300, (Nov. 2006).

(Continued)

*Primary Examiner* — Paul Zarek
(74) *Attorney, Agent, or Firm* — Oblon, Spivak, McClelland, Maier & Neustadt, L.L.P.

(57) ABSTRACT

Provided are a marker for determining sensitivity to an anti-cancer agent capable of distinguishing a therapeutic response of an individual patient and a novel means for a cancer therapy using the marker. The marker for determining sensitivity to an anticancer agent contains a substance in a metabolic pathway in which L-phenylalanine and/or N,N-dimethyl glycine are/is involved.

12 Claims, 3 Drawing Sheets

(56) References Cited

OTHER PUBLICATIONS

Sorensen, M. Nanna et al., "TIMP-1 is Significantly Associated with Ojective Response and Survival in Metastatic Colorectal Cancer Patients Receiving Combination of Irinotecan, 5-Fluorouracil, and Folinic Acid", Clin., Cancer Res., vol. 13, No. 14, pp. 4117-4122, (Jul. 15, 2007).

Paradiso, Angelo at al., "Topoisomerase-I, Thymidylate Synthase Primary Tumour Expression and Clinical Efficacy of 5-FU/CPT-11 Chemotherapy in Advance Colorectal Cancer Patients", Int., J., Cancer, vol. 111, pp. 252-258, (2004).

Extended Search Report issued Jun. 7, 2011 in European Patent Application No. 09705658.4-1223 / 2237042.

Mary A. Hilton, et. al., "Plasma Amino Acids During High-Dose Methotrexate-Citrovorum "Rescue"", Biochemical Medicine, XP023071575, vol. 16, No. 1, Aug. 1, 1976, pp. 9-15.

Eri Arita, et al., "Metabolomic Screening for Blood Biomarkers to Predict Sensitivity to CPT-11 by using CE-TOFMS", Proceedings of the American Association for Cancer Research Annual Meeting, XP008136748, vol. 49, Apr. 2008, p. 1139.

TE Sawyer, et al., "The Interaction of Buthionine Sulphoximide (BSO) and the Topoisomerase I Inhibitor CPT-11", British Journal of Cancer, XP008136794, vol. 74, No. Suppl. 27, 1996, pp. S109-S113.

Written Opinion issued Oct. 25, 2012 in Singaporean Application No. 201005341-1.

N. R. Belton, et al., "Measurement of phenylalanine in routine care of phenylketonuric children", Archives of Disease in Childhood, vol. 48 (6), 1973, pp. 472-475.

European Office Action issued Jun. 15, 2012, in Patent Application No. 09 705 658.4.

"Fluke Chemika-BioChemika", Fluka Chemie AG, 1993, p. 1041.

U.S. Appl. No. 14/007,145, filed Sep. 24, 2013, Tanigawara, et al.

Extended European Search Report issued Dec. 11, 2013 in Patent Application No. 13005363.0.

Robert H. Allen, et al., "Serum Betaine, $N,N$-Dimethylglycine and $N$-Methylglycine Levels in Patients With Cobalamin and Folate Deficiency and Related Inborn Errors of Metabolism" Metabolism, vol. 42, No. 11, XP026327682, Nov. 1, 1993, pp. 1448-1460.

\* cited by examiner

MARKER FOR DETERMINATION OF SENSITIVITY TO ANTI-CANCER AGENT

TECHNICAL FIELD

The present invention relates to a marker for determining sensitivity to an anticancer agent which is used to determine whether a cancer in a subject patient has a therapeutic response to an anticancer agent or not, and to an application thereof.

BACKGROUND ART

There are various kinds of anticancer agents such as an alkylating agent, a platinum agent, an antimetabolite, an antitumor antibiotic, and an antitumor plant alkaloid. In addition, those anticancer agents exhibit the effects in some cases and exhibit no effect in other cases, which depends on the kind of cancer. However, it is known that, even if the cancer is a kind in which an anticancer agent is confirmed to be effective, the anticancer agent exhibits the effect in some cases and exhibits no effect in other cases, leading to interindividual differences. Whether an anticancer agent exhibits the effect on the cancer of an individual patient or not is designated to as sensitivity to the anticancer agent.

Irinotecan hydrochloride (CPT-11) is an anticancer agent developed in Japan, and has a mechanism of antitumor action based on the inhibition of topoisomerase I. In Japan, CPT-11 indicated for non-small-cell lung cancer, small cell lung cancer, cervical cancer, and ovarian cancer was approved as an effective drug in January 1994. Further, CPT-11 indicated for gastric cancer, colorectal cancer, breast cancer, squamous cell carcinoma, and malignant lymphoma was approved in July 1995. CPT-11 in multi-drug therapy has been recognized to be one of standard chemotherapy, in particular, as a first-line and a second-line for colorectal cancer all over the world, and CPT-11 had established the efficacy (Non-patent Documents 1 to 6).

In the chemotherapy for advanced or metastatic colorectal cancer, the combination of a key drug such as CPT-11 or oxaliplatin that launched in 1990's, and a fluoro-pyrimidine preparation as typified by fluorouracil (5-FU), which had been a main drug for a colorectal cancer therapy before the launches of the key drug, was used, whereby clinical performance including a survival rate has been improved dramatically. Nevertheless, it is the present situation the objective response rate is about 500, and the half of patient to which an anticancer agent was administered with high risks such as serious adverse events have not achieved the response. There is urgent need to establish a marker for predicting sensitivity to an anticancer agent for use in determining interindividual therapeutic response (responder/non-responder).

In general, the treatment schedule of cancer chemotherapy extends for a long period, and whether the objective response is achieved or not and whether the administration must be continued or not are determined after some courses of therapy were repeated monitoring for adverse events. However, it is the fact that along time has passed and a high health care cost has been charged until that time, and the adverse events have been also expressed. Therefore, if there is a means for predicting whether the effect can be obtained or not for individual patients in the earlier stage of the therapy, the burden of the patients and the expression of the adverse events can be alleviated, and the health care cost can be reduced.

CPT-11 itself has an antitumor activity and is activated by carboxyl esterase in a body to thereby be converted into 7-ethyl-10-hydroxycamptothecin (SN-38) having 100 to several thousands times stronger antitumor activity compared to that of CPT-11. It is thought that the coexistence of CPT-11 and SN-38 simultaneously in a body leads to the antitumor effect. SN-38 is glucuronidated by UDP-glucuronosyltransferase (UGT) in a liver cell and becomes an SN-38 glucuronate conjugate (SN-38G) having no cytotoxicity. Then, SN-38G is mainly excreted in the bile and transferred to the intestine, and thereafter, excreted in the stool. A part of SN-38G excreted in the intestine is subjected to metabolism and excretion while undergoing the following steps: SN-38G is deconjugated by β-glucuronidase of enteric bacteria, and becomes an active SN-38 again; and the active SN-38 is reabsorbed through a transporter in the intestinal epithelium, and is subjected to the enterohepatic circulation and glucuronate conjugation by UGT in an intestinal epithelial cell, and the like (Non-patent Document 7). In this case, SN-38 may damage intestinal mucosa and induce diarrhea. In addition, it is recognized that SN-38 influences bone marrow where active cell division occurs, to thereby induce erythrocytopenia, leukocytopenia, and thrombocytopenia.

It is demonstrated that the change in the exposure amount of SN-38 in a body caused by genetic polymorphism of UGT1A1 is one reason for the adverse effects such as serious diarrhea and neutropenia. However, because of the complexity disposition, for example, the conversion of CPT-11 as a prodrug into SN-38 as an active metabolite and detoxication thereof, the reproduction of SN-38 in the process of enterohepatic circulation, and the metabolism of CPT-11 itself and the production of SN-38 from the metabolite, there has been no report that the therapeutic effect can be predicted by pharmacokinetics. There is also reported that the expression level of the mRNA of carboxyesterase in a peripheral mononuclear cell is correlated with an AUC ratio of SN-38 and SN-38G but not correlated with a tumor reduction effect (Non-patent Document 8).

On the other hand, as a factor related with sensitivity or resistance to CPT-11, there is reported involvement of: the presence or absence of the mutation of topoisomerase I as a target of SN-38 and the expression level thereof; carboxylesterase activity involved in the conversion of CPT-11 into SN-38 (Non-patent Document 9); and a transporter (multidrug resistance protein (MRP)-1, MRP-2, or Breast cancer resistant protein (BCRP)/ABCG2) which influences the accumulation amount of CPT-11 or SN-38 in cells. In addition, a cell proliferation antigen Ki-67, a tumor suppressor gene p53, and the like are also studied on the correlation with the response to a therapy using CPT-11. In vitro, there has been most recently attempted to predict sensitivity to an anticancer agent systematically by combining the anticancer agent sensitivity data and the microarray data, and for camptothecin derivatives, topotecan has been studied (Non-patent Document 10). In clinical research, there has been recently reported that the plasma level of tissue inhibitor of metalloproteinase-1 (TIMP-1), the TIMP-1 having an anti-apoptosis action, is correlated significantly with the clinical prognosis of a therapy using CPT-11 and 5-FU in combination for metastatic colorectal cancer (Non-patent Document 11). Thus, the necessity of a biomarker for predicting sensitivity to CPT-11 is recognized and many researches have been carried out. However, there is reported that it has not been confirmed that both topoisomerase I as a target and thymidylate synthase as a factor for predicting sensitivity to 5-FU have a definite correlation with the therapeutic response to the therapy using 5-FU and CPT-11 in combination (Non-patent Document 12). No definite biomarker capable of predicting a therapeutic response has been established.

RELATED ART DOCUMENTS

[Non-patent Document 1] J Clin Oncol 1993; 11: 909-913.
[Non-patent Document 2] Semin Oncol 1999; 26 (1 Suppl 5): 6-12.
[Non-patent Document 3] Lancet 1998; 352: 1407-1412.
[Non-patent Document 4] Pro ASCO 2005; Abstract #3506.
[Non-patent Document 5] N Engl J Med 2000; 343: 905-914.
[Non-patent Document 6] Lancet 2000; 355: 1041-1047.
[Non-patent Document 7] Cancer Res 1991; 51: 4187-4191.
[Non-patent Document 8] Clin Cancer Res 2005; 11: 6901-6907.
[Non-patent Document 9] Pharmacogenet Genomics 2007; 17: 1-10.
[Non-patent Document 10] Nat Med 2006; 12: 1294-1300.
[Non-patent Document 11] Clin Cancer Res 2007; 13: 4117-4122.
[Non-patent Document 12] Int J Cancer 2004; 111: 252-258.

DISCLOSURE OF THE INVENTION

Problems to be solved by the Invention

An object of the present invention is to provide a marker for determining sensitivity to an anticancer agent capable of determining therapeutic response of individual patients and to provide a novel means for a cancer therapy using the marker.

Means for solving the Problems

The inventors of the present invention searched a marker for determining sensitivity to an anticancer agent through a comprehensive analysis of the serum metabolome (integral of total metabolite) of in vivo cancer-bearing mice by using capillary electrophoresis time-of-flight mass spectrometry (CE-TOFMS). Two kinds of human colorectal cancer cell lines having different sensitivities to SN-38 were each transplanted into a nude mouse. As a result of study, the inventors found that the amount of a metabolite, whose concentration increases specifically in the cancer-transplanted mouse group, decreased to that of a control group only in the high sensitivity group by a CPT-11 therapy. Further, the metabolite was found to be L-phenylalanine and/or N,N-dimethyl glycine. The inventors further studied based on the finding, and have found that: whether the cancer of a cancer patient has sensitivity to an anticancer agent or not can be determined by measuring the concentration of a substance in a metabolic pathway in which L-phenylalanine and/or N,N-dimethyl glycine are/is involved in a biological sample derived from the cancer patient; the use of the expression inhibition of the substance as an index enables the screening of an agent for enhancing sensitivity to an anticancer agent (hereinafter referred to as "anticancer agent sensitivity-enhancing agent"); and the therapeutic effect of the anticancer agent is remarkably improved by using the anticancer agent sensitivity-enhancing agent and the anticancer agent as a target of the sensitivity enhancement in combination. Thus, the present invention has been completed.

That is, the present invention provides a marker for determining sensitivity to an anticancer agent, containing a substance in a metabolic pathway in which L-phenylalanine and/or N,N-dimethyl glycine are/is involved.

The present invention also provides a method of determining sensitivity to an anticancer agent, including measuring, in a specimen, a concentration of a substance in a metabolic pathway in which L-phenylalanine and/or N,N-dimethyl glycine are/is involved.

The present invention also provides a kit for carrying out the method of determining sensitivity to an anticancer agent, containing a protocol for measuring, in a specimen, a concentration of a substance in a metabolic pathway in which L-phenylalanine and/or N,N-dimethyl glycine are/is involved.

The present invention also provides a method of screening an anticancer agent sensitivity-enhancing agent, including using, as an index, an expression inhibition of a substance in a metabolic pathway in which L-phenylalanine and/or N,N-dimethyl glycine are/is involved.

The present invention also provides an anticancer agent sensitivity-enhancing agent, which is obtained by the above method of screening.

The present invention also provides a composition for cancer therapy, containing a combination of the above anticancer agent sensitivity-enhancing agent and an anticancer agent as a target of sensitivity enhancement.

The present invention also provides use of a combination of the above anticancer agent sensitivity-enhancing agent and an anticancer agent as a target of sensitivity enhancement, for producing a therapeutic drug for cancer.

The present invention also provides a method of treating cancer, including administering the above anticancer agent sensitivity-enhancing agent and an anticancer agent as a target of sensitivity enhancement.

Effects of the Invention

If the marker for determining sensitivity to an anticancer agent of the present invention is used, the therapeutic response of individual patients to the anticancer agent can be appropriately determined before the administration of the anticancer agent or in the early stage after the administration of the anticancer agent is started. As a result, an anticancer agent having high therapeutic effect can be selected, whereby the progression of the cancer and the enhancement of the adverse events due to the continuous administration of the anticancer agent whose therapeutic effect cannot be expected can be prevented. Further, the reduction in the burden of the patients and the reduction in the health care cost can also be expected. Further, if the marker is used, an anticancer agent sensitivity-enhancing agent can be screened. A cancer therapeutic effect is remarkably improved by using the anticancer agent sensitivity-enhancing agent and the anticancer agent as a target thereof in combination.

BEST MODE FOR CARRYING OUT THE INVENTION

One of the marker for determining sensitivity to an anticancer agent of the present invention is a substance in a metabolic pathway in which L-phenylalanine is involved (also referred to as "L-phenylalanine metabolic pathway substance"). Examples of the substance include, in addition to L-phenylalanine, all substances which increase the concentration of L-phenylalanine in a metabolic pathway, and a substance enhancing the metabolism to L-phenylalanine, and a substance inhibiting the metabolism from L-phenylalanine are exemplified. Here, examples of the substance enhancing the metabolism to L-phenylalanine include an intermediate in a metabolic pathway from a protein or a peptide to L-phenylalanine, an enzyme involved in the metabolism, a coenzyme thereof, and a substance changing the expression level or the activity of the enzyme. In addition, examples of the substance inhibiting the metabolism from L-phenylalanine include an inhibitor of L-phenylalanine metabolic enzyme, a substance decreasing the expression level or the activity of the L-phenylalanine metabolic enzyme, and a coenzyme of the L-phenylalanine metabolic enzyme. Of those, L-phenylalanine is particularly preferred.

The other marker for determining sensitivity to an anticancer agent of the present invention is a substance in a metabolic pathway in which N,N-dimethyl glycine is involved (also referred to as "N,N-dimethyl glycine metabolic pathway substance"). Examples of the substance include, in addition to N,N-dimethyl glycine, all substances which increase the concentration of N,N-dimethyl glycine in a metabolic pathway, and a substance enhancing the metabolism to N,N-dimethyl glycine, and a substance inhibiting the metabolism from N,N-dimethyl glycine are exemplified. Here, examples of the substance enhancing the metabolism to N,N-dimethyl glycine include an intermediate in a metabolic pathway from a phospholipid to N,N-dimethyl glycine, an enzyme involved in the metabolism, a coenzyme thereof, and a substance changing the expression level or the activity of the enzyme. In addition, examples of the substance inhibiting the metabolism from N,N-dimethyl glycine include an inhibitor of N,N-dimethyl glycine metabolic enzyme, a substance decreasing the expression level or the activity of the N,N-dimethyl glycine metabolic enzyme, and a coenzyme of the N,N-dimethyl glycine metabolic enzyme. Of those, N,N-dimethyl glycine is particularly preferred.

The concentrations/concentration of L-phenylalanine and/or N,N-dimethyl glycine increased in the serum of a mouse in which cancer cells had been transplanted, compared to that of a cancer cell-non-transplanted group as described in Examples below. In addition, in the group in which HT-29, a cancer cell line having low sensitivity to SN-38, had been transplanted, the concentrations/concentration of L-phenylalanine and/or N,N-dimethyl glycine did not decrease even after the administration of CPT-11. On the contrary, in a group in which HCT-116, a cancer cell line having high sensitivity to SN-38, had been transplanted, the concentrations/concentration of L-phenylalanine and/or N,N-dimethyl glycine decreased after the administration of CPT-11 to the same degree as those/that of the control group. Accordingly, L-phenylalanine and/or N,N-dimethyl glycine are/is effective as a marker for determining sensitivity to an anticancer agent such as CPT-11, SN-38, or the like.

The anticancer agent serving as a subject of the marker for determining sensitivity to an anticancer agent of the present invention is not particularly limited, as long as the anticancer agent is one affecting the metabolic pathway of L-phenylalanine and/or N,N-dimethyl glycine. Examples of the anticancer agent include CPT-11, SN-38, oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Of those, a plant alkaloid-derived anticancer agent such as CPT-11, SN-38, or salts thereof is preferred.

When the sensitivity to an anticancer agent is determined using the marker for determining sensitivity to an anticancer agent of the present invention, the concentrations/concentration of an L-phenylalanine metabolic pathway substance and/or an N,N-dimethyl glycine metabolic pathway substance in a specimen may be measured. Here, examples of the specimen include a biological sample derived from a subject having cancer (cancer patient), such as blood, serum, plasma, urine, tumor tissue, tumor cell, ascitic fluid, pleural fluid, cerebrospinal fluid, stool, or expectoration. The serum is particularly preferred.

In addition, examples of the target cancer in the present invention include lip, oral, and pharyngeal cancers typified by pharyngeal cancer; gastrointestinal cancers typified by esophageal cancer, gastric cancer, and colorectal cancer; respiratory and intrathoracic organ cancers typified by lung cancer; bone and articular cartilage cancers; malignant melanoma, squamous cell carcinoma of skin and other cancer of skin; mesothelial and soft tissue cancers typified by mesothelioma; female genital cancers typified by breast cancer, uterine cancer, and ovarian cancer; male genital cancers typified by prostate cancer; urinary tract cancers typified by bladder cancer; eye, brain, and central nervous system cancers typified by brain tumor; thyroid cancer and other endocrine cancers; lymphoid tissue, hematopoietic tissue, and related tissue cancers typified by non-Hodgkin's lymphoma and lymphoid leukemia; and metastatic cancers, primary focuses of which are those cancers. The present invention can particularly suitably be used for non-small-cell lung cancer, small cell lung cancer, cervical cancer, ovarian cancer, gastric cancer, colorectal cancer, squamous cell carcinoma of skin, and malignant lymphoma.

Means for measuring the concentration of the L-phenylalanine metabolic pathway substance or N,N-dimethyl glycine metabolic pathway substance in a specimen may be determined appropriately according to the target substance to be measured. For example, the concentration can be measured by CE-TOFMS, gas chromatography-mass spectrometry (GC-MS), HPLC, an immunological measurement method, a biochemical measurement method, or the like. In the case of L-phenylalanine, the concentration can be measured quantitatively by CE-TOFMS, HPLC, a biochemical measurement method, or the like. In particular, the quantitative measurement by an enzymatic method using fluorescent intensity is easy. In the case of N,N-dimethyl glycine, the concentration can be measured quantitatively by CE-TOFMS, HPLC, GC-MS, or the like.

For determining sensitivity to a target anticancer agent, the concentrations/concentration of the L-phenylalanine metabolic pathway substance and/or the N,N-dimethyl glycine metabolic pathway substance in a biological sample derived from a cancer patient are/is measured before and after the administration of the anticancer agent. If the concentrations/concentration of the L-phenylalanine metabolic pathway substance and/or the N,N-dimethyl glycine metabolic pathway substance before and after the administration of the anticancer agent does not change, the cancer can be determined not to have sensitivity to the anticancer agent. In the case where the concentrations/concentration of the L-phenylalanine metabolic pathway substance and/or the N,N-dimethyl glycine metabolic pathway substance after the administration of the anticancer agent decrease/decreases compared to those/that before the administration of the anticancer agent, the cancer can be determined to have sensitivity to the anticancer agent.

In addition, in the case where, before the administration of the anticancer agent or in the early stage after the administration thereof, the concentrations/concentration of the L-phenylalanine metabolic pathway substance and/or the N,N-dimethyl glycine metabolic pathway substance are/is determined to be higher than the predetermined standard concentration, the cancer can be determined not to have sensitivity to the target anticancer agent. In the case where the cancer does not have sensitivity to the target anticancer agent, the drug effect thereof cannot be expected. In this case, if the administration of the anticancer agent whose drug effect cannot be expected continues, there is a fear of the advance of the cancer or the enhancement of the adverse events. Thus, the marker for determining sensitivity to an anticancer agent of the present invention greatly contributes to not only the determination of the therapeutic response to the anticancer agent but also the prevention of the enhancement of the adverse events accompanied by the continuous administration of the anticancer agent whose drug effect cannot be expected.

In order to carry out the method of determining sensitivity to an anticancer agent of the present invention, it is preferred to use a kit containing a protocol for measuring the concentrations/concentration of the L-phenylalanine metabolic pathway substance and/or N,N-dimethyl glycine metabolic pathway substance in a specimen. The kit contains a reagent for measuring the concentrations/concentration of the L-phenylalanine metabolic pathway substance and/or N,N-dimethyl glycine metabolic pathway substance, directions for use of the measurement reagent, a standard for determining the presence or the absence of sensitivity to the anticancer agent, and the like. The standard refers to the standard concentrations/concentration of the L-phenylalanine metabolic pathway substance and/or the N,N-dimethyl glycine metabolic pathway substance, a concentration which is determined to be high or low, a factor influencing the measurement result, the degree of the influence, and the like. Those concentrations can be set for each target anticancer agent. By using the standard, the determination can be performed as described above.

By using the expression inhibition of the L-phenylalanine metabolic pathway substance and/or the N,N-dimethyl glycine metabolic pathway substance as indexes/an index, an anticancer agent sensitivity-enhancing agent can be screened. That is, in vitro or in vivo, a substance inhibiting the expression of the L-phenylalanine metabolic pathway substance and/or the N,N-dimethyl glycine metabolic pathway substance enhances sensitivity to the anticancer agent. For example, before and after the administration of an anticancer agent to a cancer-bearing animal, a substance enhancing the decrease in the concentrations/concentration of the L-phenylalanine metabolic pathway substance and/or N,N-dimethyl glycine metabolic pathway substance is a substance enhancing sensitivity to the anticancer agent (anticancer agent sensitivity-enhancing agent). A substance decreasing the concentrations/concentration of the L-phenylalanine metabolic pathway substance and/or N,N-dimethyl glycine metabolic pathway substance in various kinds of cancer cell lines in vitro in the presence of an anticancer agent is a substance enhancing sensitivity to the anticancer agent (anticancer agent sensitivity-enhancing agent).

In addition, by using the L-phenylalanine metabolic pathway substance and/or N,N-dimethyl glycine metabolic pathway substance as indexes/an index, an anticancer agent can be screened. That is, in vitro or in vivo, if the concentrations/concentration of the L-phenylalanine metabolic pathway substance and/or N,N-dimethyl glycine metabolic pathway substance are/is decreased by a substance, the substance is an anticancer agent. For example, if, after a substance is administered to a cancer-bearing animal, the concentrations/concentration of the L-phenylalanine metabolic pathway substance and/or N,N-dimethyl glycine metabolic pathway substance decrease/decreases, the substance is an anticancer agent. In addition, if, in vitro, after a substance is exposed to various kinds of cell lines, the concentrations/concentration of the L-phenylalanine metabolic pathway substance and/or N,N-dimethyl glycine metabolic pathway substance decrease/decreases compared to those/that before the exposure, the substance is an anticancer agent. In the case of an anticancer agent expected to have a drug effect, the decrease in the concentrations/concentration of the L-phenylalanine metabolic pathway substance and/or N,N-dimethyl glycine metabolic pathway substance appears earlier than reduction in the size of the tumor or a cell-killing effect. Therefore, by screening which uses the L-phenylalanine metabolic pathway substance and/or N,N-dimethyl glycine metabolic pathway substance as indexes/an index, whether the substance is effective as an anticancer agent or not can be determined by investigation for a shorter period. A great effect can also be expected from the viewpoint of the reduction in labor and cost accompanying the development of an anticancer agent.

If the thus obtained anticancer agent sensitivity-enhancing agent and an anticancer agent as a target of the sensitivity enhancement are used in combination, the therapeutic effect of the anticancer agent is remarkably improved. The form of the combination of the anticancer agent sensitivity-enhancing agent and an anticancer agent as a target of the sensitivity enhancement may be a composition containing the components of both agents, or may be a combination of separate preparations. In addition, those components may be administrated through different routes. Examples of the anticancer agent used here and serving as a subject are the same as those described above, and include CPT-11, SN-38, oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Of those, a plant alkaloid-derived anticancer agent such as CPT-11, SN-38, or salts thereof is particularly preferred.

EXAMPLES

Next, the present invention is described in more detail by way of examples.

Example 1

(1) Method (a) Animal

Six-week-old, male nude mice (BALB/cAJcl-nu/nu) purchased from CLEA Japan, Inc. were used and allowed to ingest a general feed and drink water freely in a thermostatic chamber. A protocol following the animal experiment guideline in School of Medicine, Keio University was applied and then approved. Then, this examination was carried out humanely.

(b) Cultured Human Colorectal Cancer Cells

Cultured human colorectal cancer cells, HCT-116, having high sensitivity to SN-38 and cultured human colorectal cancer cells, HT-29, having low sensitivity to SN-38 were obtained from Yakult Honsha, Co., Ltd.

(c) Drug

CAMPTO™ as a preparation of CPT-11 and a solvent for dissolving Campto (hereinafter, referred to as "solvent") were obtained from Yakult Honsha, Co., Ltd.

(d) Production of Cancer-Bearing Mouse and Sample Collection

The cultured human colorectal cancer cells, HT-29, having low sensitivity to SN-38 or the cultured human colorectal cancer cells, HCT-116, having high sensitivity to SN-38 were subcutaneously transplanted on the back of each 6-week-old nude mouse in an amount of 2,000,000 cells/100 µL/mouse. After the transplantation, a tumor size was measured by using the following formula: (longer tumor diameter)×(shorter tumor diameter)$^2$/2. When the tumor size reached 300 to 400 mm$^3$, the mice were randomly assigned to a CPT-11 administration group and a solvent administration group (a CPT-11 non-administration group). The day when the mice were assigned to two groups was defined as day 0. CAMPTO™ as a preparation of CPT-11 in an amount of 4.5 mL/kg (90 mg/kg as CPT-11 amount) and the solvent for dissolving CAMPTO™ (D-sorbitol, lactic acid, pH adjuster) were administered slowly to the CPT-11 administration group and a CPT-11 non-administration group, respectively, from the tail vein. The tumor size was measured on day 0, and 12 hours, 24 hours, 72 hours, and 7 days after the administration. The blood was collected after the dissection. After the centrifugation of the collected blood at 10,000 rpm for 10 minutes, a serum fraction was frozen with liquid nitrogen and stored at −80° C. until the serum fraction was used in preparation of a sample for metabolome analysis. As a control group, a cancer cell-non-transplanted group was produced and the same treatment was carried out.

(e) Preparation of Metabolome Sample

A serum stored at −80° C. after the dissection of a mouse, was plunged into a methanol solution containing an internal standard (IS), and then the proteins were denatured. After that, chloroform and milli-Q water were added to carry out a liquid-liquid extraction, whereby contaminants were removed. A water-methanol layer including metabolites was separated, and was then centrifugally filtered through 5,000 kDa cutoff filter to remove proteins. After that, the filtrate was dried under reduced pressure and stored at −80° C. The dried resultant was dissolved in milli-Q water immediately before the measurement and subjected to a metabolome measurement.

(f) Metabolome Measurement

The comprehensive measurement of the metabolites in a serum was carried out by using a capillary electrophoresis time-of-flight mass spectrometry (CE-TOFMS) system manufactured by Agilent Technologies, Inc. In this examination, a voltage was applied such that an output of the capillary was a cathode, and cationic metabolites were comprehensively measured.

(g) Analysis Method

The obtained peaks were subjected to automatic extraction by using Molecular Feature Extractor (Agilent Technologies, Inc.) which is an automatic peak extraction software, in the following conditions: m/z, 50 to 1,000; RT, 0 to 50 minutes; and S/N ratio, 2 or more. The m/z value was plotted on the abscissa and the IS ratio as peak intensity on the ordinate on Microsoft Excel™. The analysis method included plotting m/z values on the abscissa on Microsoft Excel™ with a small interval and confirming the difference of the expression levels one by one.

(2) Results

Figure 1:
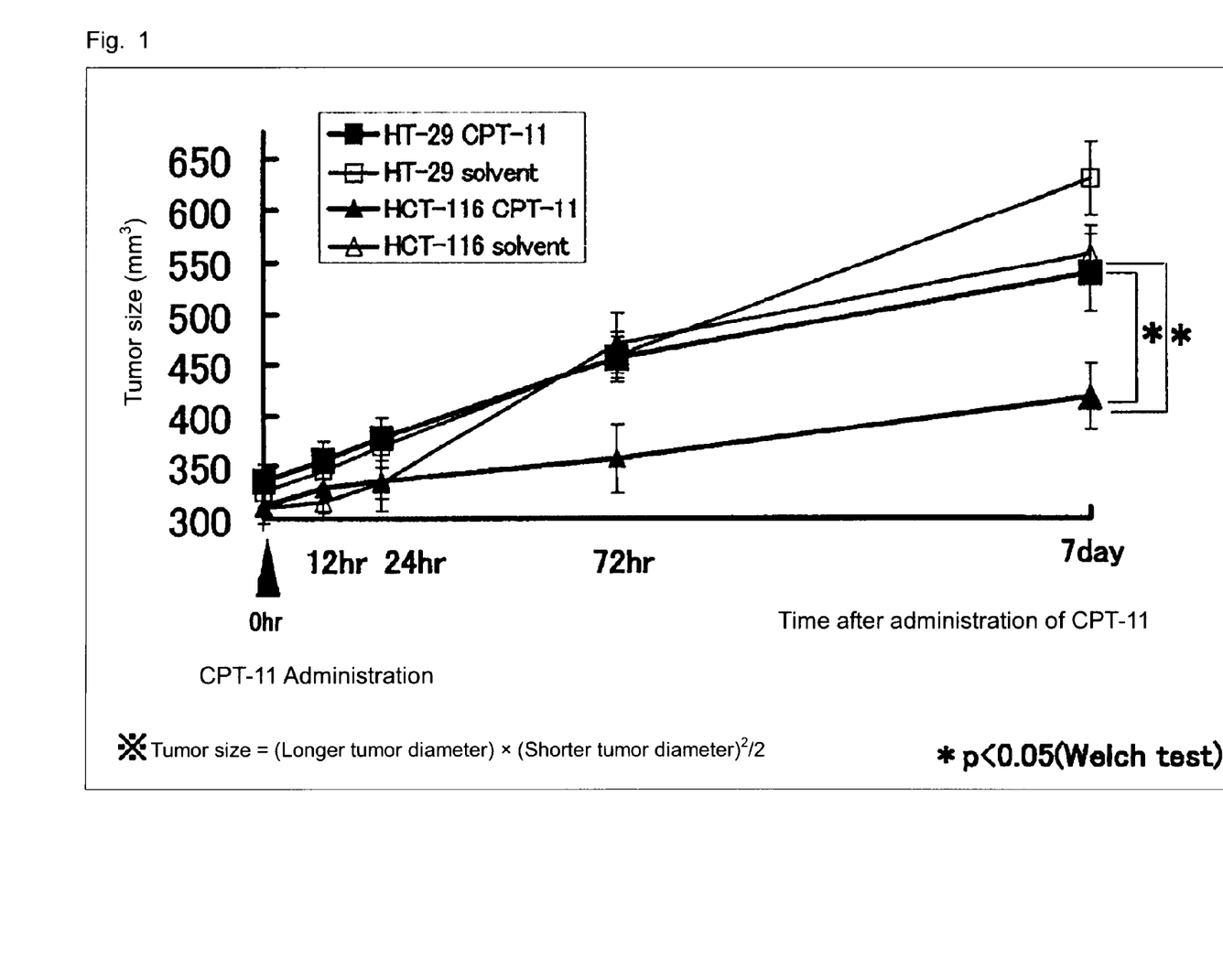
FIG. 1 is a graph illustrating chronological changes in tumor size of cancer-bearing mice in each group.

The cultured human colorectal cancer cells, HCT-116, having high sensitivity to SN-38 or the cultured human colorectal cancer cells, HT-29, having low sensitivity to SN-38 were transplanted on the back of each nude mouse. After the transplantation, a tumor size was measured by using the following formula: (longer tumor diameter)×(shorter tumor diameter)$^2$/2. When the tumor size reached 300 to 400 mm$^3$, the mice were randomly assigned to a CPT-11 administration group and a solvent administration group. The tumor size was measured on day 0, and 12 hours, 24 hours, 72 hours, and 7 days after the administration. FIG. 1 illustrates the results. 7 days after the administration, there was a significant difference (p=0.01319) between a CPT-11 administration group and a solvent administration group (a CPT-11 non-administration group) in which the cultured human colorectal cancer cells, HCT-116, having high sensitivity to SN-38 had been transplanted In addition, there was also a significant difference (p=0.04979) between a CPT-11 administration group in which the cultured human colorectal cancer cells, HCT-116, having high sensitivity to SN-38 had been transplanted and a CPT-11 administration group in which the cultured human colorectal cancer cells, HT-29, having low sensitivity to CPT-11 had been transplanted Thus, it was confirmed that the cultured human colorectal cancer cells, HCT-116, used in this examination has high sensitivity to CPT-11 compared to the cultured human colorectal cancer cells, HT-29, and on the contrary, the cultured human colorectal cancer cells, HT-29, has low sensitivity to CPT-11 compared to the cultured human colorectal cancer cells, HCT-116.

Figure 2:
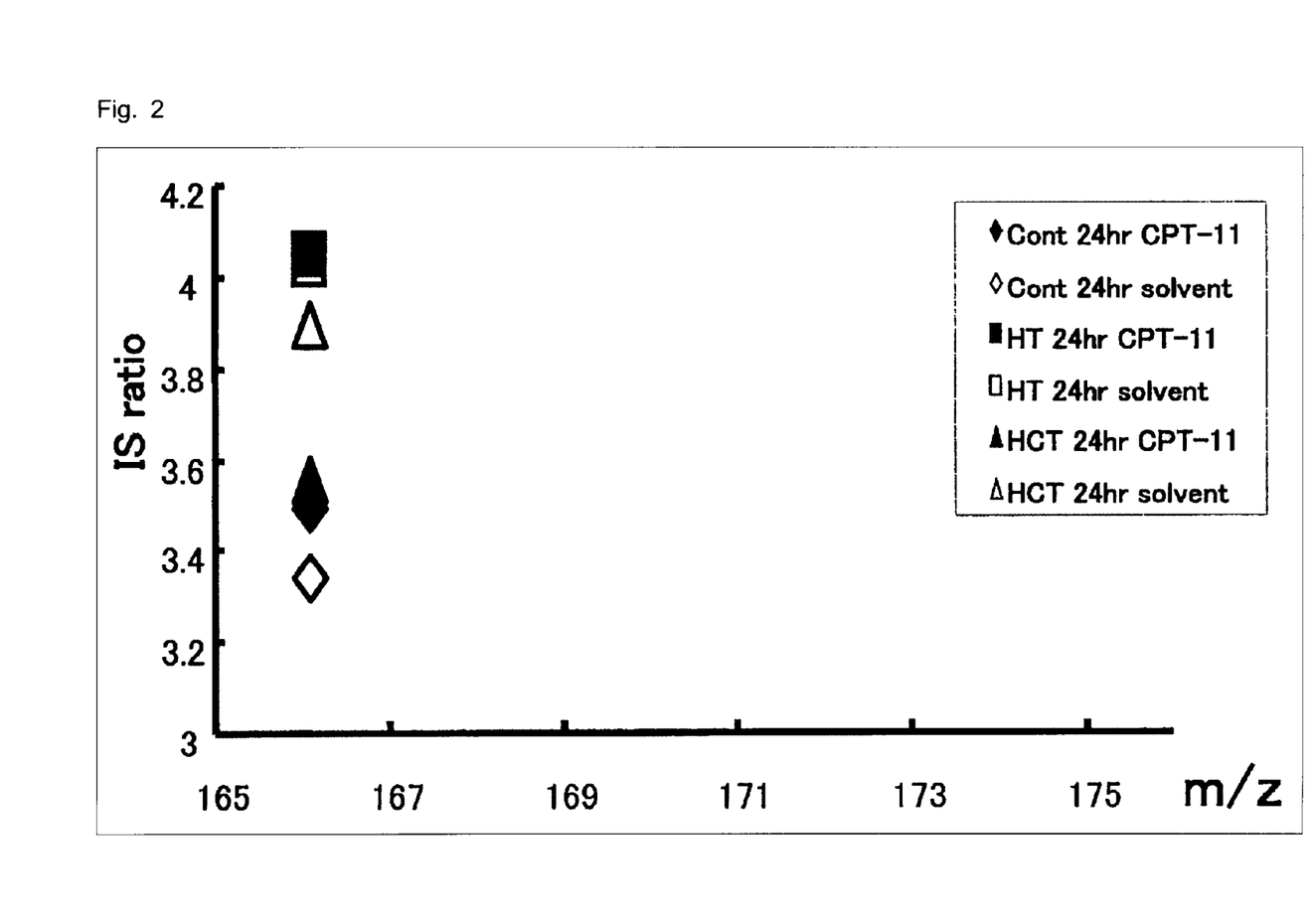
FIG. 2 is a graph illustrating serum phenylalanine concentrations (m/z 166.086) in nude mice 24 hours after the administration of CPT-11 in a control group in which no cancer cell was transplanted (Cont), a group in which cultured human colorectal cancer cells, HT-29, having low sensitivity to SN-38 were transplanted (HT), and a group in which cultured human colorectal cancer cells, HCT-116, having high sensitivity to SN-38 were transplanted (HCT).
Figure 3:
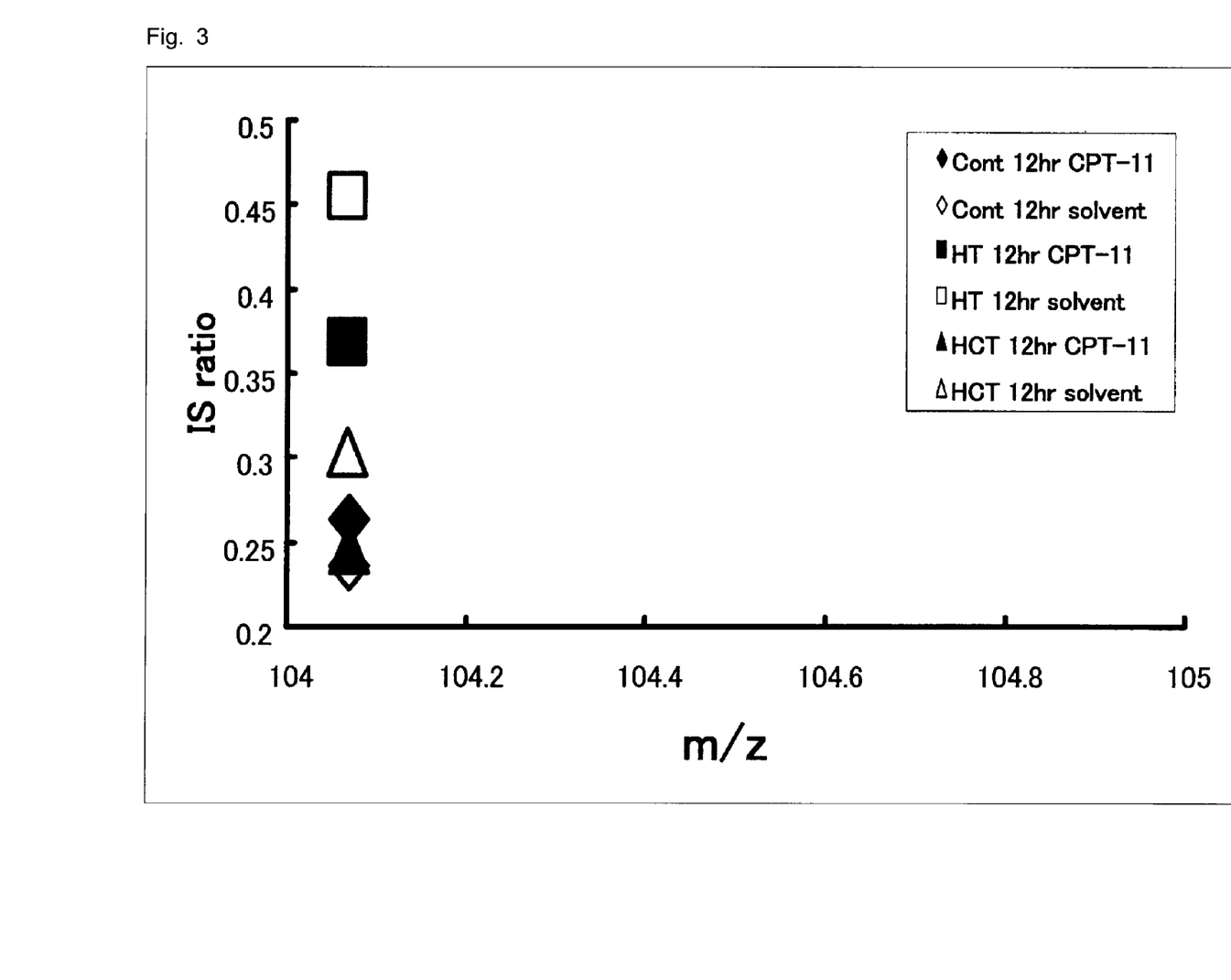
FIG. 3 is a graph illustrating serum N,N-dimethyl glycine concentrations (m/z 104.070) in nude mice 12 hours after the administration of CPT-11 in a control group in which no cancer cell was transplanted (Cont), a group in which cultured human colorectal cancer cells, HT-29, having low sensitivity to SN-38 were transplanted (HT), and a group in which cultured human colorectal cancer cells, HCT-116, having high sensitivity to SN-38 were transplanted (HCT).

The average number of peaks detected per sample was 263. The change patterns of individual peaks were analyzed by visual observation and the peaks of the candidates which can be a biomarker exhibiting drug response to CPT-11 were obtained. Those peaks of the candidates were a peak at m/z of 166.086 obtained by measuring the metabolites in a serum 24 hours after the administration of CPT-11 or the solvent (FIG. 2) and a peak at m/z of 104.070 obtained by measuring the metabolites in a serum 12 hours after the administration of CPT-11 or the solvent (FIG. 3).

Regarding the peak at m/z of 166.086, the expression levels in the serum of CPT-11 administration group and solvent administration group (CPT-11 non-administration group) at 24 hours after the administration of the agent were the same level in cancer-bearing mice in which the cultured human colorectal cancer cells, HT-29, having low sensitivity to SN-38 had been transplanted. However, in cancer-bearing mice in which the cultured human colorectal cancer cells, HCT-116, having high sensitivity to SN-38 was transplanted, the peak expression level in the serum of CPT-11 administration group decreased to the same level as in the control group in which no cancer cell had been transplanted at 24 hours after the administration of the agent. Therefore, the groups were able to be separated into a CPT-11 ineffective group and a CPT-11 effective group, and the metabolite was presumed to be a marker exhibiting a drug response. Regarding the peak, a molecular formula was predicted by using an analysis software Analyst™ QS (Applied Biosystems, Inc.). The molecular formula was determined from the isotope ratio with respect to a parent peak and information such as accurate mass. As a result, the molecular formula of the candidate peak at m/z of 166.086 was found to be $C_9H_{12}NO_2$. A substance predicted from the molecular formula was searched by using a metabolism database of KEGG: Kyoto Encyclopedia of Genes and Genomes (http://www.kegg.jp/) produced by Kyoto University, with the result that the substance showing the peak was proved to be L-phenylalanine.

Regarding the peak at m/z of 104.070, the expression levels in the serum of CPT-11 administration group and solvent administration group (CPT-11 non-administration group) at 12 hours after the administration of the agent were the same level in cancer-bearing mice in which the cultured human colorectal cancer cells, HT-29, having low sensitivity to SN-38 had been transplanted. However, in cancer-bearing mice in which the cultured human colorectal cancer cells, HCT-116, having high sensitivity to SN-38 had been transplanted, the peak expression level in the serum of CPT-11 administration group decreased to the same level as in the control group in which no cancer cell had been transplanted at 12 hours after the administration of the agent. Therefore, the groups were able to be separated into a CPT-11 ineffective group and a CPT-11 effective group, and the metabolite was presumed to be a marker exhibiting a drug response. Regarding the peak, a molecular formula was predicted by using an analysis software Analyst™ QS (Applied Biosystems, Inc.). The molecular formula was determined from the isotope ratio with respect to a parent peak and information such as accurate mass. As a result, the molecular formula of the candidate peak at m/z of 104.070 was found to be $C_4H_9NO_2$. A substance predicted from the molecular formula was searched by using a metabolism database of KEGG: Kyoto Encyclopedia of Genes and Genomes (http://www.kegg.jp/) produced by Kyoto University, with the result that four kinds of candidate compounds were obtained. By an additional test using a pure compound from commercial sources, the substance showing the peak was proved to be N,N-dimethyl glycine.

The invention claimed is:
1. A method of determining sensitivity of colorectal cancer to an anticancer agent, comprising
 (a) obtaining a biological sample from a subject having colorectal cancer;
 (b) measuring a concentration of at least one marker selected from the group consisting of L-phenylalanine and N,N-dimethyl glycine in said biological sample obtained in (a);
 (c) administering to said subject an anticancer agent selected from the group consisting of irinotecan, a salt of irinotecan, SN-38, and a salt of SN-38;
 (d) obtaining a biological sample from said subject following said administering;
 (e) measuring a concentration of at least one marker selected from the group consisting of L-phenylalanine and N,N-dimethyl glycine in said biological sample obtained in (d);
 (f) comparing the concentration of said at least one marker measured in (e) to the concentration of said at least one marker measured in (b) to determine whether said colorectal cancer is sensitive to said anticancer agent.
2. The method according to claim 1, wherein said marker is L-phenylalanine.
3. The method according to claim 1, wherein the anticancer agent is irinotecan or a salt thereof.
4. The method according to claim 1, wherein the anticancer agent is SN-38 or a salt thereof.
5. The method according to claim 1, wherein in (f)
 when the concentration of said at least one marker in (e) is greater than the concentration of said at least one marker in (b), the colorectal cancer is not sensitive to said anticancer agent;
 when the concentration of said at least one marker in (e) is the same as than the concentration of said at least one marker in (b), the colorectal cancer is not sensitive to said anticancer agent; and
 when the concentration of said at least one marker in (e) is less than the concentration of said at least one marker in (b), the colorectal cancer is sensitive to said anticancer agent.
6. The method according to claim 1, wherein said marker is N,N-dimethyl glycine.
7. A method of determining whether an anticancer drug would provide a therapeutic response in a subject having colorectal cancer, comprising
 (a) obtaining a biological sample from a subject having colorectal cancer;
 (b) measuring a concentration of at least one marker selected from the group consisting of L-phenylalanine and N,N-dimethyl glycine in said biological sample obtained in (a);
 (c) administering to said subject an anticancer agent selected from the group consisting of irinotecan, a salt of irinotecan, SN-38, and a salt of SN-38;
 (d) obtaining a biological sample from said subject following said administering;
 (e) measuring a concentration of at least one marker selected from the group consisting of L-phenylalanine and N,N-dimethyl glycine in said biological sample obtained in (d);
 (f) comparing the concentration of said at least one marker measured in (e) to the concentration of said at least one marker measured in (b) to determine whether said anticancer agent would provide a therapeutic response in said subject.
8. The method according to claim 7, wherein said marker is L-phenylalanine.

9. The method according to claim 7, wherein the anticancer agent is irinotecan or a salt thereof.

10. The method according to claim 7, wherein the anticancer agent is SN-38 or a salt thereof.

11. The method according to claim 7, wherein in (f)
when the concentration of said at least one marker in (e) is greater than the concentration of said at least one marker in (b), the anticancer agent does not provide a therapeutic effect;
when the concentration of said at least one marker in (e) is the same as than the concentration of said at least one marker in (b), the anticancer agent does not provide a therapeutic effect; and
when the concentration of said at least one marker in (e) is less than the concentration of said at least one marker in (b), the anticancer agent provides a therapeutic effect.

12. The method according to claim 7, wherein said marker is N,N-dimethyl glycine.

* * * * *